United States Patent [19]

DeFoney et al.

[11] 4,039,653

[45] Aug. 2, 1977

[54] LONG-ACTING ARTICLES FOR ORAL DELIVERY AND PROCESS

[75] Inventors: George F. DeFoney, Philadelphia; Donald S. Mayes, Sunbury, both of Pa.; Henry S. Brenman, Cinnaminson, N.J.

[73] Assignee: DeFoney, Brenman, Mayes & Baron, Cinnaminson, N.J.

[21] Appl. No.: 597,696

[22] Filed: July 21, 1975

Related U.S. Application Data

[62] Division of Ser. No. 435,940, Jan. 23, 1974, Pat. No. 3,911,199.

[51] Int. Cl.$^2$ .................. A61K 9/22; A61K 9/24; A61K 9/50; A61K 9/52
[52] U.S. Cl. .................. 424/19; 128/260; 424/20; 424/21; 424/22; 424/28; 424/14; 424/16
[58] Field of Search .................. 424/14, 16, 19–22, 424/48, 49; 128/260, 268; 252/316

[56] References Cited

U.S. PATENT DOCUMENTS

| 3,053,255 | 9/1962 | Meyer | 128/268 |
|---|---|---|---|
| 3,137,631 | 6/1964 | Soloway | 252/316 X |
| 3,339,546 | 9/1967 | Chen | 128/156 |
| 3,429,308 | 2/1969 | Russell | 128/1 |
| 3,444,858 | 5/1969 | Russell | 128/260 |
| 3,495,988 | 2/1970 | Balassa | 252/316 X |
| 3,516,941 | 6/1970 | Matson | 252/316 |
| 3,598,123 | 8/1971 | Zaffaroni | 128/268 |
| 3,731,683 | 5/1973 | Zaffaroni | 128/268 |
| 3,742,951 | 7/1973 | Zaffaroni | 128/268 |
| 3,797,494 | 3/1974 | Zaffaroni | 128/268 |

FOREIGN PATENT DOCUMENTS

2,311,042   9/1973   Germany

OTHER PUBLICATIONS

Chem. Abstr. 80, No. 63850z, (1974), of Grimm Ger. Offen. 2,311,042, Sept. 20, 1973, "Micro-Encapsulated Flavors for Dentrifices."

*Primary Examiner*—Shep K. Rose
*Attorney, Agent, or Firm*—James Albert Drobile; Robert S. Bramson

[57] ABSTRACT

Long-acting capsules or tablets containing materials for masking odors of the oral cavity or for introducing medications into the oral cavity or for introducing medications into the oral cavity in human beings and other animals and comprising suitable pharmaceutically acceptable odor masking or medicament substances in encapsulated form and present in a capsule, tablet or other article of such size and shape or of such material as to allow the article to reside for prolonged periods of time of at least one hour in adjacent contact with the oral mucosa.

1 Claim, 5 Drawing Figures

LONG-ACTING ARTICLES FOR ORAL DELIVERY AND PROCESS

REFERENCE TO RELATED CASES

This is a division of Application Ser. No. 435,940 filed Jan. 23, 1974, now U.S. Pat. No. 3,911,199.

BACKGROUND OF THE INVENTION

1. Field of the Invention

The invention relates to new and useful articles capable of being inserted in the oral cavity of humans or other animals and releasing gradually over a prolonged period of time, medicaments or odor-masking substances which will mask any foul or unpleasant odors emanating from the oral cavity. Process for masking such oral odors or introducing medication in the oral cavity.

2. State of the Art

Processes for sustained released encapsulation of medicaments, including medicaments in liquid form, are well known in the art. Also, compositions for masking odors emanating from the oral cavity of humans and other animals are well known in the art. These odor-masking compositions are typically presented in such forms as mouth washes, breath sprays, breath deodorant chewing gums, and the like.

The foregoing prior art compositions and products have not been effective in providing sustained release of odor-masking substances or medicaments in the oral cavity of humans and other animals for periods of one or more hours, for several reasons. In some instances, the substances are presented in liquid form, without any sustained release condition, and are merely washed away by the secretions of the oral mucosa and have a residence time in the oral cavity of no more than several minutes. In the case of such substances as deodorant chewing gums, the deodorant constituents are not in sustained release form, and once the deodorant coating of the chewing gum is broken, it dissolves in a relatively short period of time, i.e., on the order of one-half hour or less, and does not have any truly sustained release effect. Moreover, such prior art devices as chewing gum could not comfortably be placed in the area of the oral mucosa above the upper gums or below the lower gums, where they could comfortably reside for periods of hours providing sustained release effect without interfering with speech, chewing, smoking and the like, being uncomfortable, being easily released from position or otherwise being inadequate to perform a prolonged deodorant function.

BRIEF SUMMARY OF THE INVENTION

The invention comprises compositions and articles for providing odor-masking substances or medications, in liquid or particulate form, in a sustained release vehicle, and in a physical configuration or with a suitable adhesive which will allow the article containing the odor-masking substances or medicaments to remain in a relatively fixed position adjacent to or adhered to the oral mucosa in humans or other animals. This invention is also directed to a process for masking offensive odors emanating from the oral cavities of humans and other animals or introducing medicaments therein by inserting in the oral cavity odor-masking or medicating quantities of pharmaceutically acceptable deodorant or medicating materials in sustained release form in a manner by which the sustained release products are retained adjacent to the oral mucosa for periods of at least one hour and up to eight hours or even longer.

In one embodiment of the invention, a pharmaceutically acceptable adhesive is used to affix in place a tablet or microcapsules which are suitably located in a proper area of the mouth, adjacent to the oral mucosa. In another embodiment of the invention, the odor-masking or medicament substances, in a suitable sustained release vehicle, are formed into a tablet or capsule of such configuration that it will reside against the oral mucosa in a comfortable position, allowing a residence time of many hours, without being released, and without interfering with speech, eating, breathing, sleeping or like oral functions and uses. In one modification of the invention, compositions other than odor-masking materials can be utilized with the articles of the invention in order to provide sustained release dosages to the oral cavity of medications otherwise not capable of being provided in sustained release form.

OBJECTS OF THE INVENTION

It is therefore an object of this invention to provide articles capable of releasing, in the oral cavities of humans and other animals, effective quantities of odor-masking substances or medicaments during a prolonged period of time on the order of about one to about eight or more hours.

Another object of the invention is to accomplish the masking of odors or introduction of medicaments in the oral cavities over a long period of time without interfering with speech, comfort, breathing, sleeping, chewing, and like functions or uses of the oral cavity.

Yet another object of this invention is to provide a tablet or capsule containing odor-masking substances in sustained release form and in such configuration as to be able to reside comfortably in the cavities of the mouth proximate the oral mucosa without the need of adhesive.

Still another object of the invention is to provide capsules or tablets capable of comfortably residing in the corners of the mouth adjacent to the oral mucosa for prolonged periods of time by the use of a pharmaceutically acceptable adhesive.

A further object of this invention is to provide articles capable of providing sustained release of medicaments in the oral cavity without interfering with the normal functioning of the oral cavity for speech, breathing, eating, and the like.

Still another object of this invention is to provide articles which are capable of releasing local anesthetics in the oral cavity over a prolonged period of time of from one up to eight or more hours for the sustained release treatment of sore throats with local anesthetics, antihistamines, and like medicaments.

A concomitant object is to provide a process for releasing gradually in the oral cavities of humans and other animals effective quantities of odor-masking and other compositions during time periods of at least one and up to eight or more hours.

DETAILED DESCRIPTION OF THE INVENTION

Figure 1:
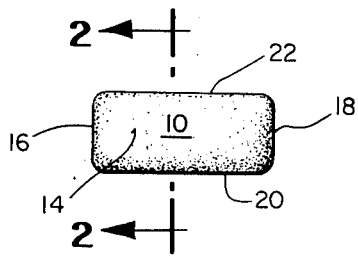
FIG. 1 is a top plan view of a preferred form of tablet in accordance with the invention.
Figure 3:
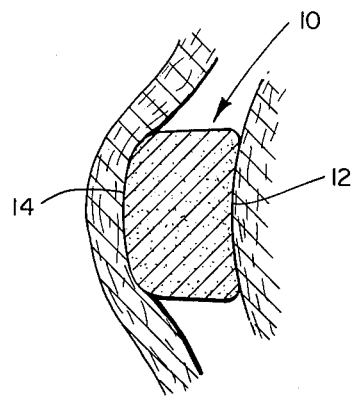
FIG. 3 is a cross-sectional view of a portion of an upper corner of the mouth, showing the tablet of FIG. 1 in its normal resident position for optimum use.

This invention relates to articles and processes for the sustained release in the oral cavity of human beings and other animals of substances, such as odor-masking substances, over prolonged periods of time. Although the preferred embodiment of the invention relates to odor-masking by the use of suitable odor-masking substances, as discussed below, it is also within the purview of this invention to utilize other substances which it is desired to release during a prolonged period of time in the oral cavity, without undue interference with the normal functions and uses of the oral cavity, such as speech, breathing, eating, sleeping, and the like, and without discomfort to the user.

In the preferred aspect of the invention, the invention is used for the masking of odors in the oral cavity of humans and other animals. The odor-masking substances which are used in the practice of the invention are usually essential oils, which are available in liquid or in powder form. The essential oils in powder form typically have been prepared in the powdered form by spray drying or adsorption, in a manner which is well known in the art. Representative essential oils usable in the practice of the invention are oil of wintergreen, peppermint oil, spearmint oil, cinnamon oil, sarsaparilla oil, clove oil, eucalyptus oil, and admixtures thereof.

These essential oils, in the practice of the invention, may be mixed with suitable extenders, flavoring agents, and the like. The types and quantities of odor-masking materials and other components which may be added thereto are virtually limitless, and the specific odor-masking materials utilized may be varied within wide ranges, so long as they are present in substantial quantities and concentrations to be able to achieve the desired odor-masking results.

In addition, it may be desired to combine with the odor-masking materials, such other ingredients as antibiotics, antiseptics analgesics, and other chemotherapeutic agents, for such applications as alleviating pain of sore throats and treating sore throats, in the manner more fully discussed below.

It is necessary that all of the ingredients of the articles of this invention be of pharmaceutically acceptable quality, so that they may be ingested by human beings and other animals without creating any health problems.

The odor-masking compositions utilized in the practice of this invention are usually available in either liquid or powdered form, and are then placed in the desired sustained-release form. There are numerous compositions and techniques available for preparing sustained release coatings, and all such compositions and techniques are within the purview of this invention, so long as they are capable of releasing, over a prolonged period of time, under the action of the liquids in the oral cavity, i.e., saliva, which is usually an alkaline or mildly acidic substance, the odor-masking or other compositions disclosed herein. The saliva of individuals can vary greatly from person to person, and can even vary substantially for particular individuals. However, the rate of solubilization of the sustained release tablets and capsules of this invention is controlled to be rather low, so that the dissolution rate is not particularly pH sensitive.

In one aspect of the invention, the odor-masking materials are desirably in liquid form and are placed in sustained release form by coacervation coating. Coacervation coating is a process which is well known to the art and is disclosed in numerous patents, such as U.S. Pat. No. 2,800,457. Coacervation coating takes liquid compositions and encapsulates them in small micro-capsules or globules, in which liquid is surrounded by a polymeric material which is a sustained release material capable of being gradually dissolved by the action of a surrounding liquid, such as the saliva in the mouth, thereby exposing the contents after dissolution of the coating.

The sustained release effect and the effect of gradual release in uniform quantities over a prolonged period of time is achieved by mixing micro-capsules having different types of coatings in a single composition. For example, the thicknesses of the coatings or the size of the capsule can be varied within wide limits, in order to provide different rates or times of dissolution of coatings in the oral cavity, and in order to provide relatively uniform release of the encapsulated compositions over a prolonged period of time. Also, different encapsulating coatings may be utilized to provide different rates and times of disintegration of the coating for varying the sustained rerelease effect. A particular product would then have predetermined amounts of different types of micro-capsules with various thicknesses or materials of coatings, in order to provide sustained release of the encapsulated materials during the predetermined time period. The selection of the particular encapsulating coatings and the manner of forming the coatings are within the purview of the skilled artisan in the field of micro-encapsulation.

Once the micro-capsules have been formed containing the desired types and thicknesses of coatings, all containing the desired odor-masking cmpositions or other medicaments, these capsules are provided with an adhesive coating, which is at least a partial coating, in order to allow the capsules to be inserted in the oral cavity where they will adhere to the oral mucosa. Therefore, in a preferred embodiment of the invention, suitable microcapsules containing odor-masking compositions are wholly or partially covered with an intraoral adhesive, which will adhere the capsules to the oral mucosa. Such adhesive must be a pharmaceutically acceptable adhesive, and a suitable adhesive is available under the trademark Oradhesive, produced by E. R. Squibb & Sons, Inc. This Oradhesive may be applied to the individual micro-capsule particles by anyone of a number of application techniques, such as by liquid deposition in a solution thereof, followed by spray drying, or by any other of the well known techniques available.

When the micro-capsule form of the invention is utilized, the invention can be dispensed as a tablet or powder, or in the form of an aerosol, in a manner which is well known in the art. In fact, if micro-capsules dispensed from an aerosol container are to be utilized, the size of the micro-capsule can be controlled to be small enough to be able to pass through the valve of the spray unit. In powdered, non-aerosol form, the micro-capsules covered with adhesive, could be poured from a suitable container in the mouth or dispensed in an aerosol in a squeeze bottle with a long dispensing nozzle. In the case of denture wearers, the micro-capsules could be dispensed directly onto dentures outside the mouth, in order to give the desired effect.

In another embodiment of the invention, the odor-masking composition or medicament, in liquid or in powder form, is incorporated into a sustained release tablet. Sustained release tablets are well kmown in the art, and different kinds of coating materials and sustained release mechanisms are available. The purpose of the sustained release tablet is to present a substantial quantity of the odor-masking composition or medicament, in powdered form, in the tablet, covered by or located within a sustained release binder or coating, which will allow the gradual release into the oral cavity of the odor-masking or other compositions at the desired rate and over a prolonged period of time, under the action of the saliva in the mouth. Suitable polymeric materials which are usable as sustained release coatings are carboxy methylcellulose, vinyl acetate resins and polyvinyl pyrillidone and salts thereof.

Figure 2:
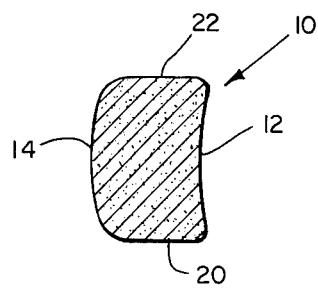
FIG. 2 is a cross-sectional view of the tablet of FIG. 1, taken along line 2—2.

In one form of the invention, the tablet, in sustained release form, is manufactured in the configuration illustrated in FIGS. 1 and 2, which is an optimum configuration for allowing the tablet to reside, without the necessary use of an adhesive, in the corners of the mouth against the oral mucosa. Viewing FIG. 2, the tablet is seen as having a curved inner surface 12 and a curved outer surface 14 which are designed to fit comfortably along the contour of the mouth at the oral mucosa. In the preferred embodiment of the invention shown in FIG. 1, the tablet will have a longitudinal dimension, from the end 16 toward the end 18 of approximately 0.75 and up to about 1.25 inches, a vertical dimension of from about 0.4 to about 0.7 inches, and a thickness of about 0.3 and up to about 0.5 inches, so that it can comfortably fit in the mouth without being unduly bulky. It is to be noted that a minimum thickness of about 0.25 inches is desirable in order to allow the tablet more readily to be held in place by the weight of the cheek. The weight of the tablet is desirably in the range from about 100 to about 700 mg. The height of the tablet, from the bottom surface 20 to the top surface 22 is most desirably approximately 0.5 inches, in order to provide an optimum size in tablet for dispensing without being unduly uncomfortable. The curvature of the tablet at the bases 12 and 14 is preferably a gradual curvature, in order to provide for optimum configuration to match the inner contour of the mouth. However, this can be varied somewhat while retaining a comfortable fit of the tablet within the mouth. It is not essential that both of the sides 12 and 14 of the tablet be curved; it is only important that the inner surface of the tablet, which is to reside against the inner face of the mouth, be curved, and the opposite surface 14 may be straight if desired. Alternatively, the two faces 12 and 14 of the tablet may be curved in opposite directions so that either face of the tablet may be properly positioned in the mouth without the necessity for turning over the tablet in the event that the wrong face is positioned against the gums. It is also to be noted that a round tablet, rather than the rectangular tablet illustrated, and having one concave and one convex face can also be utilized for a comfortable prolonged residence time in the oral cavity. Such a tablet would desirably have a diameter of from about 0.5 to about 0.8 inches.

It has been found that the use of the tablet of the above-described dimensions and configuration, will allow the tablet comfortably to reside in the upper and lower corners of the mouth, against the oral mucosa for long periods of time, on the order of up to 6 to 12 hours, without giving the user any discomfort, and without interfering with eating, breathing, sleeping, chewingg, smoking, or like functions and uses of the mouth.

In another embodiment of the invention, the tablet can be tableted in a more conventional form, designed, however, to fit comfortably within the corners of the mouth against the oral mucosa, but without the requisite shape described above and illustrated in FIGS. 1 and 2. In that event, in order to permit the tablet to remain affixed in the oral cavity for a substantially long period of time, it is desirable to use pharmaceutically acceptable oral adhesive, to adhere the tablet in the desired position. The adhesive described above, Oraadhesive, which contains pectin, gelatin, sodium carboxymethylcellulose and polyisobutylene, is the adhesive of choice. Other suitable adhesive compositions can be made from equal parts of finely powdered gelatin and petrolatum, or may include equal parts of gelatin, pectin and carboxymethylcellulose and petrolatum in an amount equal to the total of the three foregoing ingredients.

This adhesive would be fixed, in a small patch, or in spots, to the largest face of the tablet, and would be covered, in the package, with a parchment or other suitable backing, which would be removed by the user at the time it is desired to place the adhesive in the mouth. At that time, the user would take one tablet, remove the parchment backing to expose the adhesive surface, the other face of which adhesive is attached to the tablet during fabrication. The tablet is then placed in the desired location in the mouth and gently pressed against the oral mucosa. It will then remain fixed in position for the desired period of dissolution of the tablet.

After the tablet has dissolved in the mouth, the adhesive can gently, painlessly and easily be removed by the user grasping the adhesive between two fingers and gently peeling it from the mouth for suitable disposal.

The adhesive may be applied to the tablet in a rectangular or similarly shaped element having a configuration similar to the large surface of the tablet, but in somewhat smaller size than the surface of the tablet to which it is applied. Also, if desired, for economy of adhesive, the adhesive may be applied in spots along the surface of the tablet, and covered by the suitable, substantially rectangular shaped parchment or similar backing, for removal prior to application in the mouth.

Although the invention has its principal application for the purpose of a breath deodorant, to mask normal mouth odors in humans and other animals, it may be utilized for the purpose of introducing, on a sustained release basis in the oral cavity, other substances, such as medications, alone or in combination with odor-masking substances. For example, it has not heretofore been possible to provide sustained release dosages of certain medications such as amyl nitrides, for example nitroglycerin, because it is destroyed in the gastrointestinal system during any prolonged period of residence. Therefore, such medications as nitroglycerin, which must be delivered without being degraded, cannot efficiently be introduced through the gastrointestinal system. The use of the sustained release form of this invention will allow such medications to be introduced and delivered in a sustained release tablet or capsule, produced in the same manner as described herein with respect to sustained release odor-masking tablets and capsules, through the oral mucosa so that such medications can be utilized and introduced over a long period of time without degradation.

One problem in the treatment of sore throats is that the usual troches do not provide a long enough duration of medication to provide any beneficial results, since they dissolve relatively quickly and their efficacy is therefore of very short duration. By the incorporation, in accordance with this invention, of local anesthetics, such as benzocaine, or any other combination of local anesthetics desired in connection with the treatment of sore throats or comparable conditions, substantially prolonged release of these medications over a period of up to six or eight hours or more can comfortably be achieved in order to provide the prolonged relief from pain heretofore unavailable for the treatment of sore throats. These anaesthetics can be incorporated in a sustained release tablet or sustained release micro-capsules in much the same way as an oral deodorant is so incorporated.

Also, sustained release dosages of anti-caries and anti-plaque agents may be incorporated in the tablets and micro-capsules of this invention for prolonged inhibition of caries and plaque, as such agents become available for use in humans.

The articles of this invention may also contain other analgesics, such as may be utilized in connection with any oral surgery to provide long-term relief from pain in the oral cavity.

It is also important to note that, in accordance in practice of the invention, the destruction of tablets for introduction of medication normally occurring by intentional or inadvertent chewing of the tablets is avoided with the articles of this invention. Rather, by locating the articles of the invention in the corners of the mouth and by the natural bathing of the articles with the normal secretions of saliva, a steady, prolonged release of medication or oral deodorant into the oral cavity is assured.

EXAMPLE

Tablets were produced from the following ingredients:

| | |
|---|---|
| 0.85 | % by weight of magnesium stearate |
| 0.15 | % by weight of talc |
| 2 | % by weight of a 50–50 mixture of peppermint oil and spearmint oil |
| 3 | % by weight of silicon dioxide |
| 2 | % by weight of dicalcium phosphate |
| 92 | % by weight of ethylcellulose |
| 100 | % Total |

In preparing the tablet, the peppermint oil and spearmint oil were first adsorbed on the dicalcium phosphate by intimate admixture thereof in a blender. The ethycellulose was then added to the mixture and thoroughly mixed therewith. The lubricants, magnesium stearate, talc and silicon dioxide were then added and intimately admixed with the other ingredients, also in a blender. It is to be noted that the silicon dioxide acts as an adsorbent for the oils, as well as a lubricant.

The mixture was then granulated by mixing, with the gradual and intimate admixture of a pharmaceutically acceptable alcohol. The mixture was then screened by passage under pressure through a fine mesh screen. The particles were then dried and re-screened. The mixture was then formed into tablets by compressing the mixture in suitable tableting dies having the general shape illustrated in FIG. 1, which dies had been preheated to a temperature of about 130° C to about 150° C., just below the melting point of the mixture.

The tablets were then cooled and tumble coated with a water soluble gum, which is preferably 2.5% by weight of a solution of gum tragacanth in pharmaceutically acceptable shellac and 94.5% of shellac dissolved in ethanol, admixed with 3% by weight of a 50—50 mixture of peppermint oil and spearmint oil. The tumble coating adds to the tablet surface a relatively uniform deposit of the gum and oil mixture. Thus, after drying, volatilizing the alcohol, the coating comprises shellac having gum tragacanth and the peppermint and spearmint incorporated therein.

The resulting tablet will take at least 5 and up to 10 hours to dissolve in the mouth, releasing throughout its period of dissolution the odor-masking mixture of peppermint oil and spearmint oil, thereby providing a sustained release of the odor-masking oils throughout the oral cavity.

More generally, the tablet core can be formed with the following ranges of ingredients (by weight).
up to 0.85% of magnesium stearate
up to 0.15% of talc
1% to 2% of a suitable oil or mixture of oils
up to 8% of silicon dioxide
up to 10% of dicalcium phosphate
92 to 98% ethylcellulose Other lubricants, flavoring agents, extenders and suitable well-known ingredients may also be included in the tablet core.

In the coating, about 1% to about 5% by weight of a water soluble gum, such as gum tragacanth is used, and from about 2% to about 3% by weight of the essential oils. The balance is principally the shellac in alcohol solution, although other flavoring agents and like ingredients may also be added.

The foregoing tablet therefore comprises a core of odor-masking composition in ethylcellulose and a coating of a gum and additional odor-masking composition. The coating, which begins to dissolve initially, presents the initial amount of odor-masking composition for availability in the oral cavity. The ethylcellulose core material is gradually released into the oral cavity as the ethylcellulose is dissolved after part of the outside coating has been dissolved to provide access of the saliva to the tablet core.

It is to be noted that the shellac is the slowest material in the tablet to dissolve and it helps maintain the integrity of tablet, even as central core is being dissolved. Shellac is relatively unpernicious and prevents migration of the oil after formation of the tablet to provide longer shelf life.

The tablet coating thus essentially comprises particles of gum distributed throughout a matrix of shellac. Distributed throughout both gum and shellac are veins or particles of the odor-masking oil, probably in colloidal dispersion, at least in part. The gum dissolves most quickly in the saliva, thereby releasing the oils contained therein and creating channels in the shellac matrix for the entry of further saliva which dissolves the gum and, at a much slower rate, the shellac, releasing the oils into the saliva. Some of these oils migrate through the saliva in the oral cavity generally, with some equilibrium of migration probably being achieved. Thus a substantially uniform release of oil into the oral cavity is achieved. It is to be noted that the foregoing discussion of how the tablet works is theoretical only.

It is to be noted that the silicon dioxide used in the tablets of this invention is preferably in the form of fumed silica, the pharmaceutically desired form of silicon dioxide. The silicon dioxide functions both as a lubricant and as an adsorbent.

In addition to the dicalcium phosphate utilized as an adsorgent, magnesium carbonate or calcium carbonate or admixtures of dicalcium phosphate, magnesium carbonate and calcium carbonate or any other pharmaceutically acceptable diluent adsorbent may be utilized. The adsorbent is extremely important in the tablet of invention, in order uniformly to distribute the oils throughout the tablet core and to provide an additional sustained release effect for the release of the oil.

The oils that may be utilized in the tablets of the invention are any known breath-masking or odor-masking oils such as oil of wintergreen, eucalyptus oil, sarsaparilla oil, spearmint oil, peppermint oil, clove oil, cinnamon oil, and eugen oil, and admixtures thereof. Of course, all of these oils, when in use, must be in pharmaceutically acceptable form. It is also within the purview of this invention to include antiseptic agents, such a quaternary ammonium compounds, in the tablets or micro-capsules of this invention, to kill bacterial in the mouth and reduce mouth odor. Particularly useful such compounds are benzothonium chloride and acetyl trimethyl ammonium bromide.

Magnesium stearate or talc or any other pharmaceutically acceptable lubricant may be utilized in the tablets of this invention in order to facilitate the tableting operation.

The base material for the tablet, ethylcellulose, is only one of several such saliva soluble materials which may be used in the tablet of this invention, which includes carboxymethylcellulose, hydroxypropylcellulose, and methylcellulose and pharmaceutically acceptable salts thereof.

The coating material for the tablet is a water soluble gum, such as acacia or gum tragacanth, ethylcellulose, carboxymethylcellulose, cellulose acetate phthalate, hydroxypropyl cellulose, hydroxyethyl cellulose, or shellac, or combinations thereof or any other pharmaceutically acceptable gums.

The alcohols which are preferably used to dissolve the gum are any pharmaceutically acceptable alcohols, such as ethanol.

In the use of the tablet, the gum and the oils dissolve quickly in the mouth, forming interstitial channels through the tablet, permitting the ready distribution of oil from the tablet into the mouth, and allowing also for the sustained release of the odor-masking oils into the mouth.

Figure 4:
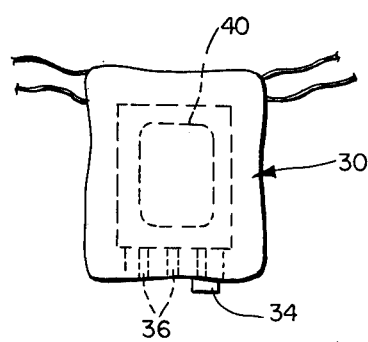
FIG. 4 is a top plan view of a false tooth having a door for containing a tablet in accordance with the invention.
Figure 5:
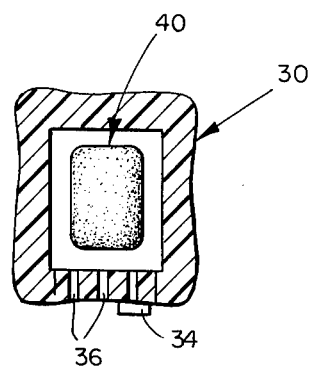
FIG. 5 is a vertical cross-sectional view of the embodiment of FIG. 4.

In the embodiment of the invention shown in FIGS. 4 and 5, the tablet of the invention is constructed to fit in a suitable cavity found in the false tooth of a set of false teeth. or in an individual crown. As seen in FIG. 5, the false tooth contains a hinged covered blank, which has a small handle which allows the cover to be opened and which latches when closed. The cover has numerous holes therein which allows saliva to gain access to the cavity blank form therein. A suitable tablet is fabricated for insertion into the false tooth and is preferably provided with different layers of odor-masking material in sustained release form, produced in the manner described above, for dissolution and release gradually in the mouth under the action of the saliva in the mouth.

It will be apparent from the above description of the invention that numerous modifications of the invention can be made without departing from the spirit and scope of the invention. For example, the particular types of odor-masking ingredients, any flavoring agents associated therewith, any medications associated therewith, and the particular type and form thereof can be varied within wide ranges using wide types of combinations of ingredients without departing from the spirit and scope of the invention.

What is claimed is:

1. A tablet for releasing a relatively uniform quantity of a medication or odor-masking material into the oral cavity of a human being or other animal over a prolonged period of time, said tablet comprising:
    a. An elongated body;
    b. Said body having at least one face having a concave curvature and adapted to fit comfortably along the upper surface of the gums at the side of the mouth;
    c. Said tablet having a surface layer encompassing said tablet comprising principally pharmaceutically acceptable shellac having medicament or essential oil admixed therein to provide substantially immediate release of medicament or odor-masking material into the oral cavity; and
    d. Said tablet having an inner core comprising principally a material selected from the group consisting of ethylcellulose, carboxymethylcellulose, methylcellulose and hydroxypropylcellulose having medicament or essential oil admixed therein for providing substantially more prolonged release of medicament or odor-masking material into the oral cavity.

* * * * *